US011805830B2

(12) United States Patent
Francisco Costa et al.

(10) Patent No.: US 11,805,830 B2
(45) Date of Patent: Nov. 7, 2023

(54) GLOVES HAVING REINFORCEMENTS AND IMPACT FEATURES

(71) Applicant: Ansell Limited, Richmond (AU)

(72) Inventors: Marco Antonio Francisco Costa, Vila Nova de Poiares (PT); Geraldo Alexandre Pimentel de Oliveira, Coimbra (PT); Paulo Alexandre Gonçalves Francisco, Vila Nova de Poiares (PT); Vasco Miguel Sousa Marques, Lorvao (PT)

(73) Assignee: ANSELL LIMITED, Victoria (AU)

( * ) Notice: Subject to any disclaimer, the term of this patent is extended or adjusted under 35 U.S.C. 154(b) by 0 days.

(21) Appl. No.: 17/833,483

(22) Filed: Jun. 6, 2022

(65) Prior Publication Data

US 2022/0295925 A1 Sep. 22, 2022

Related U.S. Application Data

(62) Division of application No. 15/245,394, filed on Aug. 24, 2016.

(60) Provisional application No. 62/209,613, filed on Aug. 25, 2015.

(51) Int. Cl.
*A41D 19/015* (2006.01)
*A41D 19/00* (2006.01)
*A61B 42/10* (2016.01)
*B29D 99/00* (2010.01)

(52) U.S. Cl.
CPC ... *A41D 19/01523* (2013.01); *A41D 19/0006* (2013.01); *A41D 19/0062* (2013.01); *A41D 19/0065* (2013.01); *A41D 19/0096* (2013.01); *A41D 19/015* (2013.01); *A41D 19/01505* (2013.01); *A61B 42/10* (2016.02); *B29D 99/0067* (2013.01)

(58) Field of Classification Search
None
See application file for complete search history.

(56) References Cited

U.S. PATENT DOCUMENTS

| 2,864,091 | A | 12/1958 | Herbert |
| 3,739,400 | A | 6/1973 | Colehower |
| 5,276,922 | A | 1/1994 | Floyd |
| 5,500,957 | A | 3/1996 | Stein |
| 6,041,438 | A | 3/2000 | Kirkwood |
| 2005/0268374 | A1 | 12/2005 | Mattesky |
| 2006/0143767 | A1 | 7/2006 | Yang et al. |
| 2008/0268374 | A1 | 10/2008 | Tashiro et al. |

(Continued)

FOREIGN PATENT DOCUMENTS

| CN | 101715307 A | 5/2010 |
| CN | 203814656 U | 9/2014 |

(Continued)

OTHER PUBLICATIONS

PCT International Search Report and Written Opinion for Application PCT/AU2016/000288 dated Nov. 28, 2016, 13 pgs.

(Continued)

*Primary Examiner* — Arti Singh-Pandey
(74) *Attorney, Agent, or Firm* — Moser Taboada

(57) ABSTRACT

Gloves comprising a polymeric coating or layer, optionally including a fabric liner, and at least one reinforcement, disposed on a part(s) of the polymeric coating or layer and/or ac part(s) of the fabric liner, and methods of making the gloves are disclosed.

9 Claims, 6 Drawing Sheets

(56) References Cited

U.S. PATENT DOCUMENTS

| | | |
|---|---|---|
| 2009/0007313 A1 | 1/2009 | Boorsma et al. |
| 2009/0070916 A1 | 3/2009 | Kassam |
| 2009/0126074 A1 | 5/2009 | Mattesky |
| 2009/0139011 A1 | 6/2009 | Vanermen et al. |
| 2010/0275342 A1 | 11/2010 | Sweeney et al. |
| 2012/0227158 A1 | 9/2012 | Ashworth et al. |
| 2013/0305430 A1 | 11/2013 | Tomono |
| 2015/0128324 A1 | 5/2015 | Baker et al. |

FOREIGN PATENT DOCUMENTS

| | | |
|---|---|---|
| FR | 2752994 A1 | 3/1998 |
| WO | WO-2009073530 A1 | 6/2009 |
| WO | WO-2015074107 A1 | 5/2015 |

OTHER PUBLICATIONS

Supplementary European Search Report dated Jan. 23, 2019 for application EP16838107.

GLOVES HAVING REINFORCEMENTS AND IMPACT FEATURES

CROSS-REFERENCE TO RELATED APPLICATIONS

This application is a divisional of U.S. application Ser. No. 15/245,394 filed Aug. 24, 2016, which issued as U.S. Pat. No. 11,425,946 on Aug. 30, 2022, and which claims the benefit of priority to U.S. Application No. 62/209,613, filed Aug. 25, 2015, both of which are incorporated herein by reference in their entirety.

BACKGROUND

Field of the Invention

Embodiments of the present invention generally relate to gloves and, more particularly, to unsupported gloves and supported gloves having an elastomeric, polymeric, or latex coating and reinforcement and/or impact features disposed thereon, and a method of making the gloves.

Description of the Related Art

Gloves are utilized in many fields for protecting workers, such as medical, industrial, household, and others. In service, gloves are subjected to extensive wear from cuts, punctures, and abrasions, creating a need for durability. Furthermore, other in-service requirements include enhanced impact resistance, grip-ability, and flexibility. Many gloves comprise fabrics and/or leathers as well as fabric/leather patches, which are bulky and expensive.

Supported gloves consist of a fabric liner that is dipped into a rubber polymer, e.g., natural rubber latex, synthetic rubber latex, and the like, forming a coating that covers at least a portion of the fabric liner. However, such gloves may not offer adequate strength in highly stressed areas. Past attempts to impart reinforcements involved the use of thick features, such as a thicker liner or a thicker polymeric feature or polymeric coating disposed thereon, any of which decrease flexibility, which leads to the tiring of hands during use.

Unsupported gloves consist of one or two layers to form a polymeric coating that is generally 0.2 mm thick. These unsupported gloves are weak, particularly in highly stressed areas, such as crotches between adjacent fingers and between the thumb and the forefinger. Attempts to strengthen unsupported gloves consist of using different polymers, which are often less flexible and/or suffer from reduced grip properties. Other attempts include making unsupported gloves that are 0.3 to 0.4 mm thick, which are less flexible and tire the hands of a user easily.

Furthermore, some supported and unsupported gloves have a foamed polymeric coating on a non-foamed polymeric coating to impart flexibility. The foamed polymeric coating may be open-celled foams or closed-celled foams. Open-celled foamed coatings absorb moisture and oils better for enhanced grip, but are commensurately weaker, i.e., not abrasion resistant, leading to breaches during use and particularly during extended use. Closed-celled foams are also weaker than non-foamed polymeric layers.

The inventors have invented supported gloves and unsupported gloves having reinforcements in particularized areas, while maintaining grip properties and methods for producing such supported gloves and unsupported gloves.

SUMMARY

Gloves comprising a polymeric coating, optionally including a fabric liner, and a reinforcement disposed on a part(s) of the polymeric coating or a part(s) of the fabric liner, and methods of making the gloves, in accordance with the present invention, substantially as shown in and/or described in connection with at least one of the figures, as set forth more completely in the claims, are disclosed. Various advantages, aspects, and novel features of the present disclosure, as well as details of an exemplary embodiment thereof, will be more fully understood from the following description and drawings.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. It is to be understood that elements and features of one embodiment may be in other embodiments without further recitation and that, where possible, identical reference numerals have been used to indicate comparable elements that are common to the figures.

DETAILED DESCRIPTION

Embodiments of the present invention include supported gloves and unsupported gloves, comprising a polymeric coating or layer and further comprising at least one reinforcement(s), which are durable, abrasion resistant and optionally impermeable. Embodiments according to the invention further include reinforcements disposed on a high stress area(s) of the gloves. High stress areas include, but are not limited to, a crotch between the thumb and forefinger, a crotch between adjacent fingers, and/or on a knuckle area(s) on the backhand of a glove. A supported glove comprises a fabric liner having a polymeric, elastomeric, or latex coating disposed thereon, and further comprising a reinforcement comprising a polyurethane material, which comprise either or both of thermoplastic or thermoset materials, disposed on the coating, creating a glove having enhanced reinforcements for strength, such as in high stress areas, such as the crotches between the index finger and thumb, or between any two fingers. Embodiments of the present invention also comprise knitted fabric liners gloves having at least one reinforcement comprised of a polyurethane material, disposed on, for example, a thumb crotch area to reinforce the crotch, forming a glove. Methods for manufacturing embodiments of the glove(s) include knitting a fabric liner, dipping the knitted fabric liner into a polymeric, elastomeric, or latex composition to dispose a coating on at least a portion of the fabric liner, curing the polymeric, elastomeric, or latex coating, and disposing the polyurethane reinforcement on the knitted fabric liner, on the coating, or on both. Similarly, an unsupported glove comprises at least one polyurethane reinforcement disposed on a polymeric, elastomeric, or latex coating or layer. Embodiments of the present invention also comprise unsupported gloves having at least one reinforcement comprised of a polyurethane material, disposed on, for example, a thumb crotch area to reinforce the glove. Embodiments of the present invention also comprise polymeric reinforcements comprising a polyurethane material and/or a polyurethane material and a nitrile-butadiene material.

Figure 1:
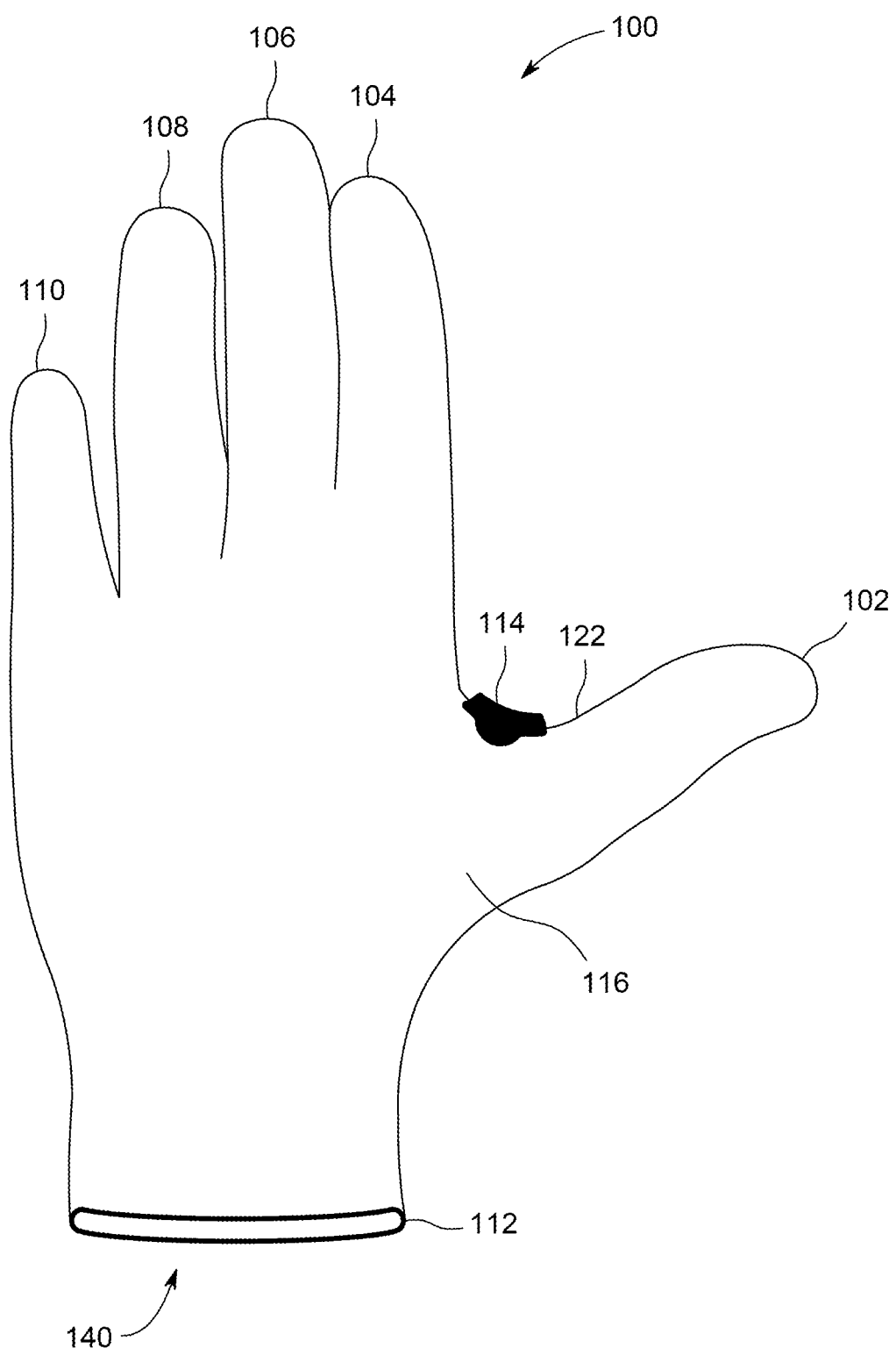
FIG. 1 depicts a perspective view of a backhand side of a lefthanded unsupported glove comprising a thumb reinforcement, according to embodiments of the present invention.

FIG. 1 depicts a perspective view of a backhand side of a lefthanded unsupported glove 100 comprising a thumb reinforcement 114, according to embodiments of the present invention. The unsupported glove 100 comprises a thumb 102, an index finger 104, a middle finger 106, a ring finger 108, a little finger 110 and, optionally, a beaded ring 112. The opening 140 is for receiving a hand of a user. The unsupported glove 100 also comprises a thumb reinforcement 114, which is located in a thumb crotch 122. The unsupported glove 100 further comprises a polymeric layer 116. The polymeric layer 116 may comprise, for example, and not limitation, an aqueous or organic solvent based polyurethane material, a nitrile-butadiene material, a highly carboxylated nitrile butadiene material, a natural rubber latex, a synthetic polyisoprene material, a polychloroprene material, and/or blends of any of the foregoing. A highly-carboxylated acrylonitrile-butadiene in this context indicates approximately 35-40% acrylonitrile, and is particularly oil-resistant for greater gripping properties. The thumb reinforcement 114 comprises a solution of a polyurethane material, as described more fully below.

Figure 2:
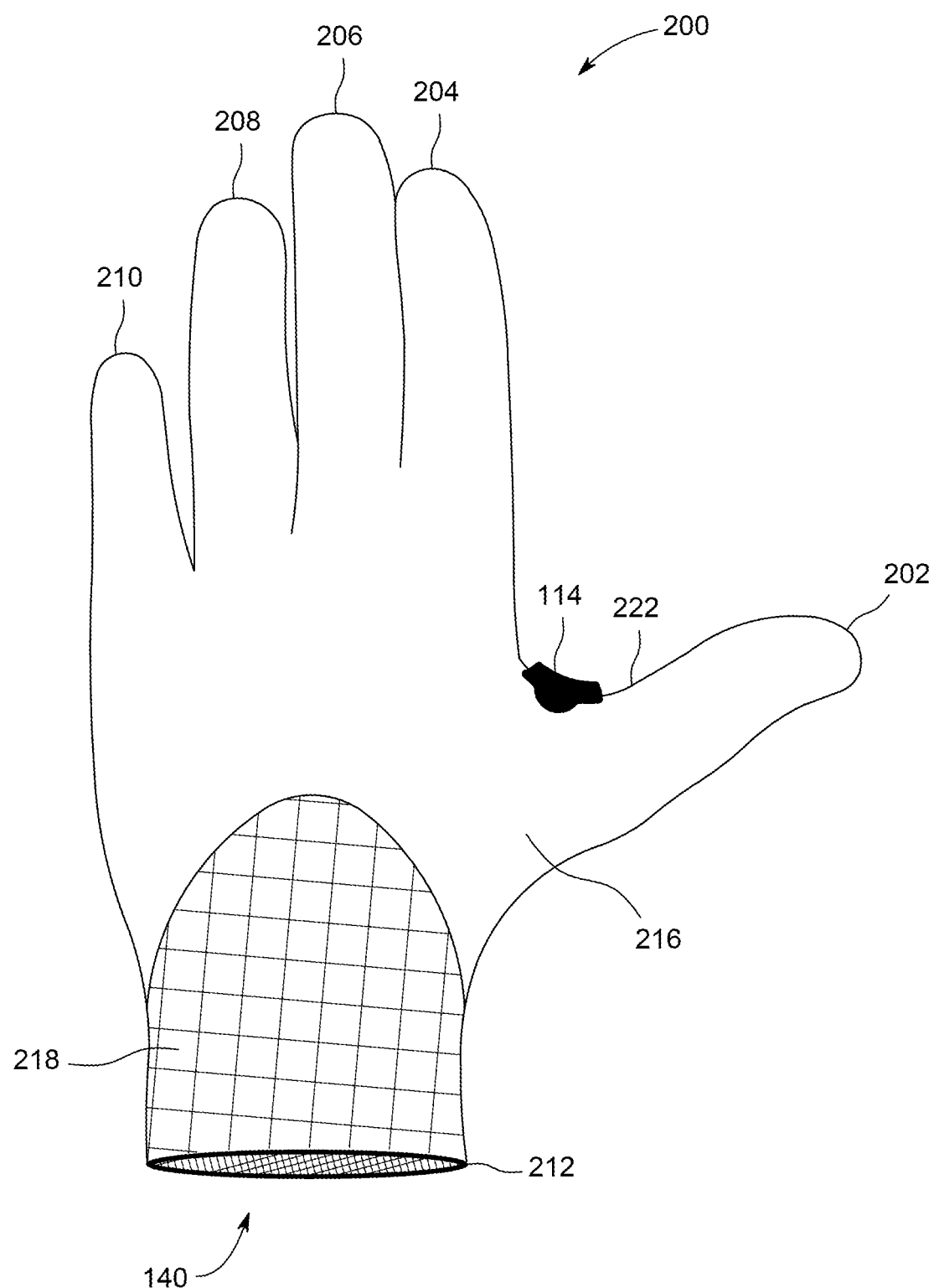
FIG. 2 depicts a backhand side of a lefthanded supported glove comprising a fabric liner having a polymeric coating and a thumb reinforcement disposed thereon according to embodiments of the invention.

FIG. 2 depicts a perspective view of a backhand side of a lefthanded supported glove 200 comprising a fabric liner 218, e.g., a knitted fabric liner, having a first polymeric coating 216 and a thumb reinforcement 114 disposed thereon according to embodiments of the invention. The supported glove 200 comprises a thumb 202, an index finger 204, a middle finger 206, a ring finger 208, a little finger 210 and, optionally, a beaded ring 212. The opening 140 is for receiving a hand of a user. The supported glove 200 also comprises a thumb reinforcement 114, comprising a polymeric material, which is located in a thumb crotch 222. In at least one exemplary embodiment, the thumb reinforcement 114 comprises an elliptical shape, having a major axis of approximately 50 mm in length that runs longitudinally along the thumb crotch 222 and a minor axis of approximately 30 mm in length, transverse to the major axis. When the supported glove 200 is worn, the thumb reinforcement 114 has the appearance of a saddle, and may be approximately 0.5 mm to 5.0 mm in thickness. The supported glove 200 further comprises a first polymeric layer 216, disposed on the knitted fabric liner 218, as a ¾ dip. In practice, the first polymeric layer 216 may be disposed as a palm dip, a ¾ dip, a knuckle dip, or a full dip as is known to those in the art. The first polymeric layer 216 comprises, for example, and not limitation, an aqueous or organic solvent based polyurethane material, a nitrile-butadiene material, a highly carboxylated nitrile butadiene material, a natural rubber latex, a synthetic polyisoprene material, a polychloroprene material, and/or blends of any of the foregoing. The thumb reinforcement 114 comprises a solution of a polyurethane material, as described more fully below.

Figure 3:
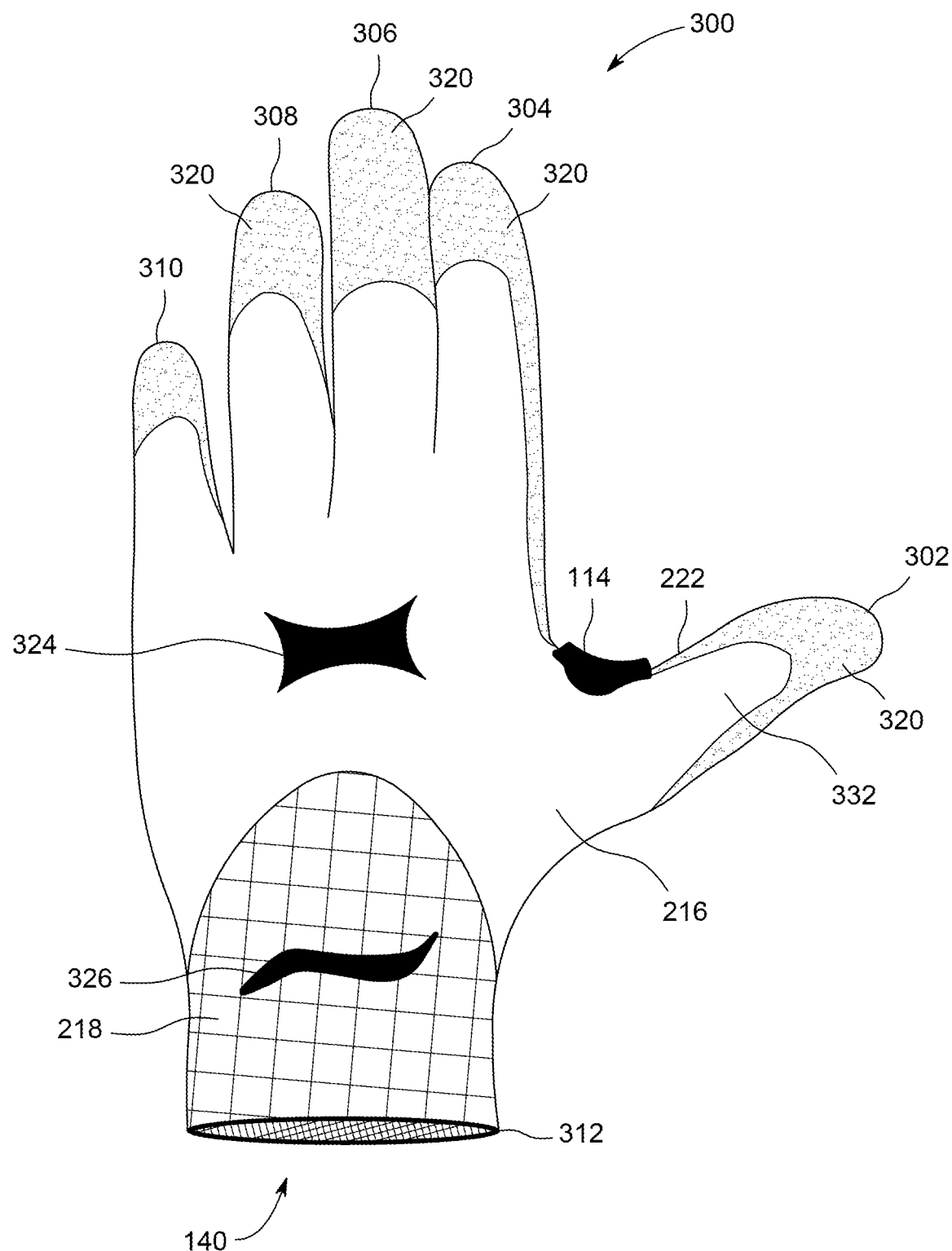
FIG. 3 depicts a backhand side of a lefthanded supported glove comprising a fabric liner having a first polymeric coating, a second polymeric coating, and a thumb reinforcement disposed thereon according to embodiments of the invention.

FIG. 3 depicts a perspective view of a backhand side of a lefthanded supported glove 300 comprising a knitted fabric liner 218 having a first polymeric coating 216, a second polymeric coating 320, and a thumb reinforcement 114, comprising a polymeric material, disposed thereon according to embodiments of the invention. The supported glove 300 comprises a thumb 302, an index finger 304, a middle finger 306, a ring finger 308, a little finger 310, and, optionally a ring 212. The opening 140 is for receiving a hand of a user. The supported glove 300 also comprises a thumb reinforcement 114, which is located in a thumb crotch 222. As shown, the first polymeric layer 216 is disposed as a ¾ dip on the knitted fabric liner 218. The second polymeric layer 320 is disposed as a knuckle dip on the first polymeric layer 216. As can be seen, the thumb reinforcement 114 traverses, and is adhered to, both the first polymeric layer 216 and the second polymeric layer 320. The thumb reinforcement 114 can be located both on the backhand side 332 and on the palm side (not shown). Also, the supported glove 300 further comprises an impact bumper 324 on the backhand side 332. And, a feature 326 is optionally adhered directly onto the knitted fabric liner 218 and being covered by the first polymeric layer 216 or second polymeric layer 320. The feature 326 is capable of, for example, resisting impacts, limiting the stretch of the knitted fabric liner, acting as a logo, and/or the like.

The first polymeric layer 216 may comprise, for example, and not limitation, an aqueous or organic solvent based polyurethane material, a nitrile-butadiene material, a highly carboxylated nitrile butadiene material, a natural rubber latex, a synthetic polyisoprene material, a polychloroprene material, and/or blends of any of the foregoing. Similarly, the second polymeric layer 320 may comprise any of those same materials or blends. The thumb reinforcement 114, or impact bumper 324 or feature 326, comprises a solution of a polyurethane material, as described more fully below, or a blend of a polyurethane material and a nitrile-butadiene material, which is optionally foamed as is known to those in the art.

Figure 4:
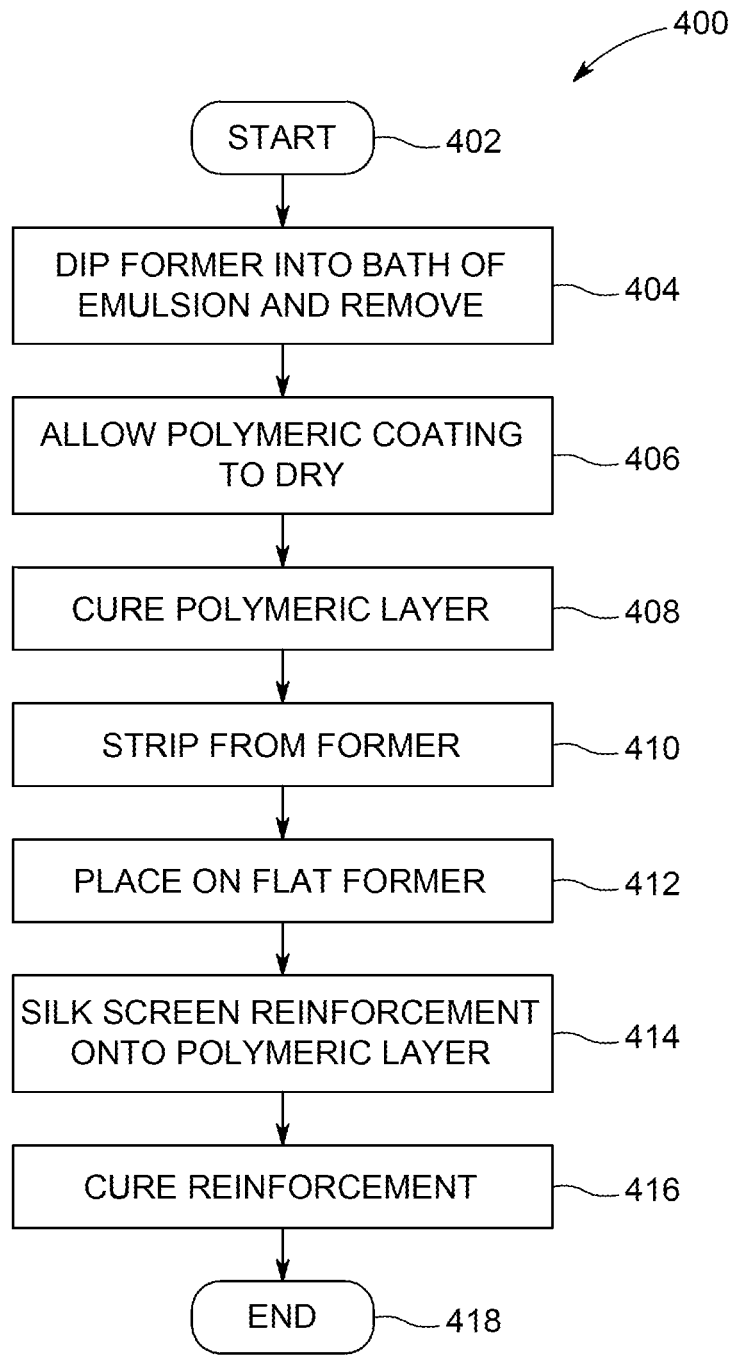
FIG. 4 depicts a flow diagram for a method for manufacturing an unsupported glove having a reinforcement, according to embodiments of the invention.

FIG. 4 depicts a flow diagram for a method for manufacturing an unsupported glove having a polymeric reinforcement, according to embodiments of the invention. The method 400 starts at 402 and proceeds to 404, at which point a former, such as a glove shaped former, is dipped into a bath of a polymeric emulsion and removed, forming an uncured polymeric layer. The polymeric emulsion comprises, for example, a polymeric, elastomeric, or latex material as described above, e.g., an aqueous or organic solvent based polyurethane material, a nitrile-butadiene material, a highly carboxylated nitrile butadiene material, a natural rubber latex, a synthetic polyisoprene material, a polychloroprene material, and/or blends of any of the foregoing.

At 406, the former is removed from the emulsion and allowed to dry as a polymeric coating on the former. At 408, the former having the polymeric coating disposed thereon is delivered to an oven so that the polymeric coating is cured, for example, at 100° C. to 150° C. for approximately 5 to 30 minutes, forming a cured polymeric layer in the shape of a glove.

At 410, the polymeric layer is optionally stripped from the former. At 412, the glove is placed within a flat former. For example, the flat former may be a bar-like former that is rounded on its tip and three sides, while being substantially flat on a side. Also, the index finger of the cured glove shaped polymeric layer may be placed over the bar-like former and the thumb of the cured glove shaped polymeric layer folded back, wherein the crotch between the thumb and the index finger is disposed on the flat area of the bar-like former.

At 414, a thumb reinforcement is made within the crotch by a silkscreening method. For example, a silkscreen of, for example, a certain mesh is placed on the flat area and a polyurethane material, or a blend of a polyurethane material and a nitrile-butadiene material, spread thereon in any reasonable shape, a circle, oval, square, rectangle, etc. Embodiments of the invention include the use of a silkscreen having a mesh size of approximately 40-61 threads per square inch. For slightly less viscous polyurethane solutions, a silkscreen having a mesh size of approximately 86 threads per square inch may be used. The polyurethane material/blend of polyurethane and nitrile-butadiene material for the thumb reinforcement may be disposed on the polymeric layer at relatively low temperatures, e.g., 15-25° C.

At 416, the polymeric layer having the thumb reinforcement on the crotch is heated and cured. In at least one embodiment of the invention, the reinforcement is cured at 140° C. for approximately 10 minutes. Also, in at least one embodiment according to the invention, an air flow of heated air at 140° C. is blown onto the thumb reinforcement at approximately 2 meters per second for approximately 5 to 30 minutes. Furthermore, for at least one embodiment according to the invention, an air flow of heated air at approximately 120° C. is blown onto the thumb reinforcement at approximately 4 meters per second or greater for approximately two to three minutes and an air flow of heated air at approximately 160° C. for approximately three to five minutes at approximately 4 meters per second, to form a cured glove having a thumb crotch reinforcement. Alternatively, the glove having the thumb crotch reinforcement may be delivered to a heated oven at approximately 180° C. for one to four minutes. At 418, the method 400 ends. Other techniques may be added to the method 400. For example, the former may have a coagulant applied and/or dried before being dipped into the emulsion. Or, the glove may be leached of impurities using water or another solvent or may be chlorinated, so that an interior and/or exterior surface is made more lubricious. Also, the glove may have a beaded ring made on a wrist portion, using techniques known to those in the art.

Figure 5:
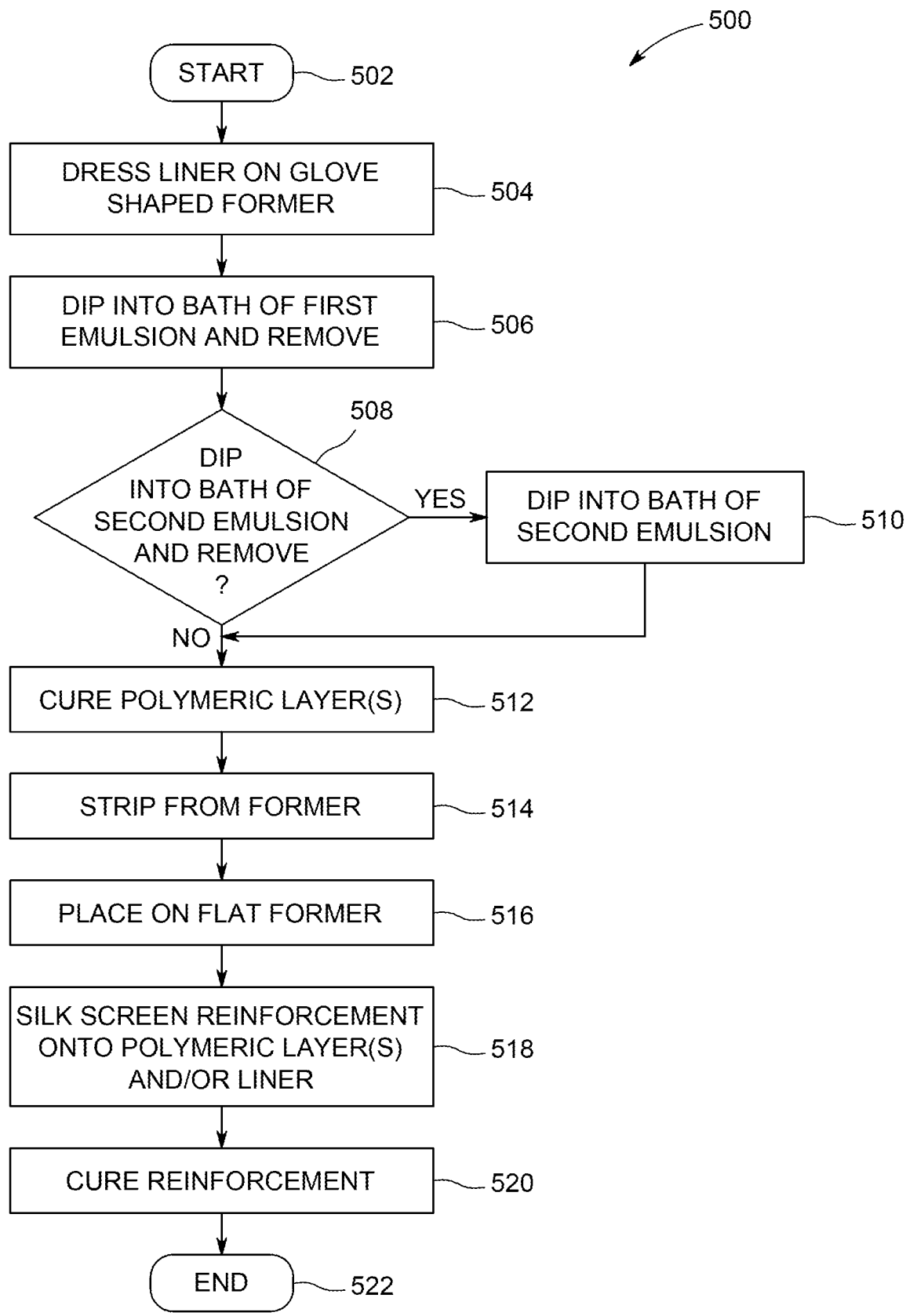
FIG. 5 depicts a flow diagram for a method for manufacturing a supported glove having a reinforcement, according to embodiments of the invention.

FIG. 5 depicts a flow diagram for a method 500 for manufacturing a supported glove having a reinforcement, according to embodiments of the invention. The method 500 starts at 502 and proceeds to 504, at which point a former, such as a glove shaped former, has a liner, such as a knitted fabric liner, dressed thereon.

At 506, the former having the liner is dipped into a bath of an emulsion and removed, forming a first uncured polymeric layer on the liner. The first uncured layer may be, for example, a knuckle-dip, a ¾ dip, a full dip, or a palm dip, etc. The emulsion may be, for example, a polymeric, elastomeric, or latex material as described above, e.g., an aqueous or organic solvent based polyurethane material, a nitrile-butadiene material, a highly carboxylated nitrile butadiene material, a natural rubber latex, a synthetic polyisoprene material, a polychloroprene material, and/or blends of any of the foregoing, as discussed above with respect to the unsupported glove.

At 508, a decision is made whether to add a second polymeric layer onto the first uncured polymeric layer. If the answer is yes, a second layer uncured polymeric layer is applied on the first uncured polymeric layer at 510 and the former is removed from a second emulsion and allowed to dry as a second polymeric coating on the first uncured polymeric layer. The second uncured polymeric layer may also be, for example, a knuckle-dip, a ¾ dip, a full dip, or a palm dip, etc. And, as above, the emulsion of which the second polymeric layer is comprised may be a polymeric, elastomeric, or latex material, e.g., an aqueous or organic solvent based polyurethane material, a nitrile-butadiene material, a highly carboxylated nitrile butadiene material, a natural rubber latex, a synthetic polyisoprene material, a polychloroprene material, and/or blends of any of the foregoing, as discussed above. The first emulsion and the second emulsion may comprise the same polymeric material or different materials. If the answer is no to the decision at 508, the method 500 proceeds directly to 512.

At 512, the former having the first uncured polymeric coating and/or second uncured polymeric layer disposed thereon is delivered to an oven so that the polymeric coating is cured, for example, at 100° C. to 150° C. for approximately 5 to 30 minutes, forming a cured polymeric layer(s) in the shape of a glove.

At 514, the polymeric layer(s) is stripped from the former. At 516, the cured polymeric layer(s) is placed within a former, which is substantially flat. For example, the flat former may be a bar-like former, as discussed above, that is rounded on its tip and three sides, while being substantially flat on at least one side. Also, the index finger of the cured glove shaped polymeric layer may be placed over the bar-like former and the thumb of the cured glove shaped polymeric layer folded back, wherein the crotch between the thumb and the index finger is disposed on the flat area of the bar-like former.

At 518, a thumb reinforcement is made within the crotch by a silkscreening method. For example, a silkscreen having a certain mesh is placed on the flat area and a polyurethane material in solution, as discussed below, spread thereon in any suitable shape, a circle, rectangle, elliptical, etc. Embodiments of the invention include the use of a silkscreen having a mesh size of the silkscreen is approximately 40-61 threads per square inch. For slightly less viscous polyurethane solutions, a silkscreen having a mesh size of the silkscreen is approximately 86 threads per square inch may be used. The polyurethane material for the thumb reinforcement may be disposed on a knitted fabric liner or one or more polymeric layer(s) at relatively low temperatures, e.g., 15-25° C. Additionally, the flat former may be positioned in any number of positions so that additional reinforcements can be added, whether to an area having the first or second polymeric layer or directly onto the liner.

At 520, the polymeric layer(s) having the thumb reinforcement on the crotch or other reinforcements, etc., is heated and cured. In at least one embodiment of the invention, the reinforcement is cured at 140° C. for approximately 10 minutes. Also, in at least one embodiment according to the invention, an air flow of heated air at 140° C. is blown onto the thumb reinforcement at approximately 2 meters per second for approximately 5 to 30 minutes. Furthermore, for at least one embodiment according to the invention, an air flow of heated air at approximately 120° C. is blown onto the thumb reinforcement at approximately 4 meters per second for approximately two to three minutes and an air flow of heated air at approximately 160° C. for approximately three to five minutes at approximately 4 meters per second or greater, to form a cured glove having a thumb reinforcement. Alternatively, the glove having the thumb reinforcement may be delivered to a heated oven at approximately 180° C. for one to three minutes. At 522, the method 500 ends.

As above, a coagulant may be applied to either or both of the knitted fabric liner and/or the first polymeric uncured layer, which may be accomplished by spraying or dipping. Also, other finishing processes may be applied. For example, where a nitrile-butadiene coating is disposed as a second polymeric coating, before curing, a salt-texturization or wrinkling processes, i.e., surface treatments, may be added to the process, as are known to those in the art, to provide enhanced grip properties. The surface treatments may further promote the adhesion of the reinforcement(s) and/or impact bumpers onto the first polymeric layer and/or second polymeric layer as discussed above.

Some steps of the method 500 may be omitted or performed in a different sequence. Also, additional steps may be employed. For example, the glove may be stripped from the former, washed, and dried. Washing can be carried out at a temperature between approximately 25° C. and 60° C., for approximately 15 to 90 minutes. The gloves may be dried in a tumble dryer for approximately 20 to 60 minutes at 50° C. to 70° C. These ranges allow different moisture contents to be imparted and/or maintained, which may be assist in manufacturing.

Figure 6A:
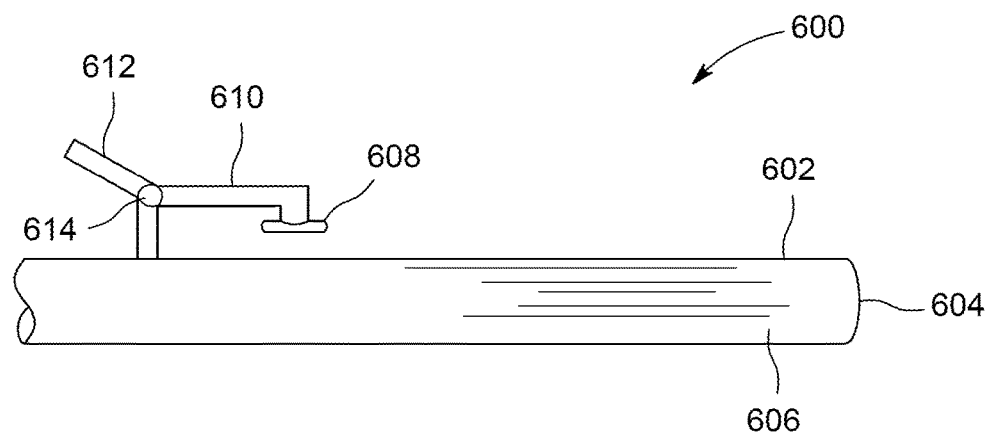
FIGS. 6A-6B depict flat formers for use in methods for manufacturing a supported glove having a reinforcement or an unsupported glove having a reinforcement, according to embodiments of the invention.

FIG. 6A depicts a flat former 600 having a clasp 610 for use in methods for manufacturing a supported glove having a reinforcement or an unsupported glove having a reinforcement, according to embodiments of the invention. The flat former 600 comprises at least one rounded surface 606, a rounded distal end 604, and at least one substantially flat surface 602. The clasp 610 further comprises a holder 608, which may be made of, for example, a rubber material so that it can provide a holding compressive force to a supported glove or an unsupported glove without risk of tearing the supported glove or the unsupported glove during silkscreening processes. The clasp 610 is biased closed by, for example, a spring 614, a ball plunger (not shown), and/or the like which may be opened by pushing a handle 612.

Figure 6B:
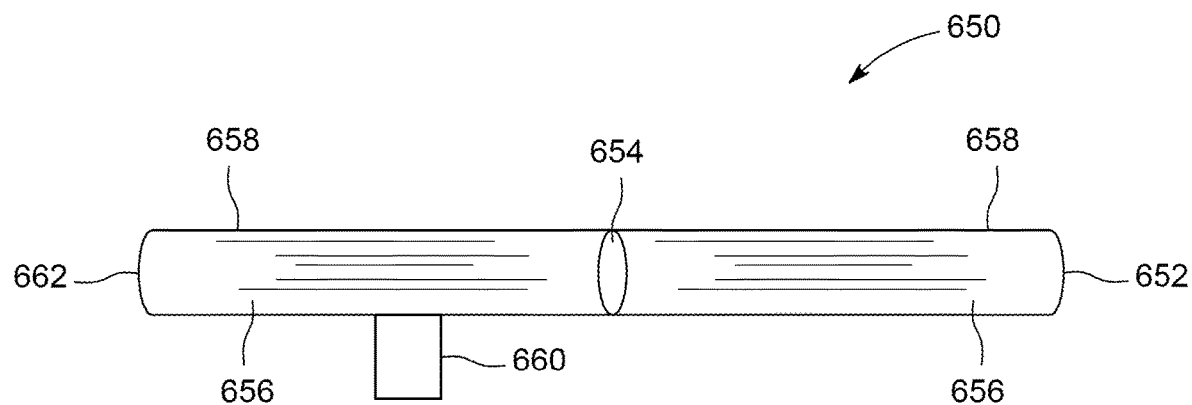

FIG. 6B depicts a hinged flat former 650 for use in methods for manufacturing a supported glove having a reinforcement or an unsupported glove having a reinforcement, according to embodiments of the invention. The hinged flat former 650 comprises a rod-like shape having a first rounded end 652 and a second rounded end 662 opposite the first rounded end 652 and having a hinge 654 disposed therebetween. Also, the hinged flat former 650 is rounded on, for example, two or more sides 656 and has at least one flat edge 658 and optionally comprises a mount 660 for mounting on, for example, a silkscreen table. A glove may be placed on the hinged flat former 650 by placing, for example, the thumb of the glove on the second rounded end 662. The first rounded end 652 is pivoted up so that it is transverse to the second rounded end 662. The first rounded end 652 is then placed within the index finger of the glove. The first rounded end 652 is then pivoted back so that it is again linear with the second rounded end 662 moderately stretching the glove flat, wherein the crotch of the glove, disposed between the index finger and the thumb, is located along the flat edge 658. A silkscreen may then be brought into contact with the crotch of the glove and the polyurethane material disposed thereon to form a reinforcement, an impact bumper, a logo, etc.

The polymeric layers and reinforcements, impact bumpers, logos, etc., discussed herein, according to embodiments of the invention, comprise natural or synthetic polymeric emulsions, compositions, mixtures, or blends thereof. For example, a polymeric coating made from an emulsion or composition may comprise a natural latex, such as guayule or natural rubber polyisoprene, synthetic latexes, such as synthetic polyisoprene, carboxylated acrylonitrile butadiene, non-carboxylated acrylonitrile butadiene, butyl latex, polychloroprene, nitriles, aqueous- and non-aqueous-polyurethanes, styrene-butadiene, and the like, or mixtures or blends thereof. Furthermore, any of the polymeric coatings and/or reinforcements, impact bumpers, logos, etc., may comprise thermosetting or thermoplastic dispersions, solutions, and/or emulsions, and/or blends thereof. Thermosetting materials may include, for example, phenolics, silicones, polyesters, and sulfur-filled (or other vulcanizing agents), vulcanizable natural and synthetic rubber materials. The inclusion of thickening agents known to those in the art to control the viscosity of the thermosetting materials is also contemplated herein.

The temperature of the polymeric emulsions and/or polyurethane solutions may be controlled, as is known in the art, and may include additives, such as surfactants, to control or modify the physical properties of the polymeric compositions and/or resulting article formed thereby. The polymeric emulsions and/or solutions also comprise various accelerants, stabilizers, pigments, and other components such as anti-microbial agents, fillers/additives, and the like. In some embodiments, the polymeric emulsions and/or solutions comprise additives, such as bentonite and other clays, minerals, silica, and/or like thickeners, to control the rheological properties of the polymeric emulsions and/or solutions. At least one suitable thixotropic agent comprises a silica, such as a fumed silica or other metal oxides. At least one exemplary fumed silica is branded as CABOSIL® by the Cabot Corporation.

The polymeric emulsions and/or solutions of one or more embodiments may also include a cure package or vulcanization agents to promote cross-linking during the curing process, such as sulfur and/or other suitable crosslinking agents and activators, such as zinc oxide, known to those in the art. The polymeric emulsions for the coatings made therefrom and/or polyurethane solutions for reinforcements, bumpers, logos, etc., often have a viscosity in the range of 250-5000 centipoises (cP) and comprise commonly used stabilizers including but not limited to potassium hydroxide, ammonia, sulfonates, and others known to those of skill in the art. In at least one exemplary embodiment, the viscosity of the polyurethane solution for the reinforcements and impact bumpers ranges from approximately 1000 cP to 40000 cP.

One exemplary formulation for a polyurethane solution for use as a reinforcement, impact bumper, or logo, as discussed above, according to embodiments of the invention, is shown in Table 1. In at least one exemplary embodiment according to the invention, the first polyurethane polymer is a high solids content aromatic polyurethane, such as LARITHANE® HS991, in an organic solvent solution. For example, one such organic solvent is an acetate, such as methoxypropyl acetate and/or an ethylene vinyl acetate. It is further contemplated that the solutions of Tables 1-3 contain no dimethyl formamide. The chain extender/crosslinker is for example, an aliphatic amine, such as LARITHANE®

HS075, and the Thickener/Rheology modifier is CABO-SIL®. The components from Table 1 are combined to form a paste, which can be disposed during the screenprinting process. In practice, many aqueous polyurethane emulsions, non-aqueous polyurethane emulsions, polyurethane-polyurea emulsions and/or polyurethane solutions can be used to form reinforcements, as well as polymeric coatings disposed on knitted fabric liners.

TABLE 1

| Component | Quantity (g) | TSC (%) |
|---|---|---|
| Solution of first polyurethane polymer | 919 | 89 |
| Chain extender/crosslinker | 81 | 100 |
| Carbon black | 50 | 100 |
| Thickener(s)/Rheology modifier(s) | 25 | 100 |

Total TSC - 90.6%

One exemplary formulation for a carboxylated nitrile-butadiene composition, suitable for producing a first or a second polymeric emulsion for disposition as a coating on a liner or another polymeric coating, according to embodiments, is shown in Table 2.

TABLE 2

| Ingredient | % in formulation |
|---|---|
| Dispersion of nitrile-butadiene polymer | 75-95 |
| Surfactant | 0-1 |
| Colorant/Pigment | 0.1-5 |
| Vulcanization agent(s) | 2-7 |
| Various additives | 0-7 |
| Thickener(s)/Rheology modifier(s) | 0.1-5 |

One exemplary formulation for a polyurethane emulsion and/or polyurethane solution, according to embodiments, disposed on the liner or another polymeric coating, is shown in Table 3. In practice, many aqueous polyurethane emulsions, non-aqueous polyurethane emulsions, and/or polyurethane-polyurea emulsions can be used to form coatings. In at least one exemplary embodiment, the formulation of Table 3 comprises 98% non-aqueous polyurethane polymer.

TABLE 3

| Ingredient | % in formulation |
|---|---|
| Dispersion of polyurethane polymer | 90-100 |
| Colorant/Pigment | 0-5 |
| Various additives | 0-3 |
| Thickener(s)/Rheology modifier(s) | 0-5 |

We have surprisingly found that polyurethane reinforcements, in addition to being spreadable as reinforcements in high stress areas, such as crotches, also have much greater grip properties than some other polymeric materials for use for some in-service applications. For example, nitrile-butadiene rubbers offer good grip properties for dry in-service requirements while polyurethanes offer good grip properties for wet and oily environments. Therefore, a glove comprising a coating of, for example, nitrile-butadiene and having polyurethane features disposed on the nitrile-butadiene coating, or vice-versa, i.e., polyurethane coating having nitrile features disposed thereon, can be used in both dry and wet/oily environments. Therefore, a user need not re-glove or even have two different types of gloves because one glove, according to embodiments of the invention, will fulfill the needs of all types. Furthermore, any of the polymeric emulsions or compositions disclosed herein, whether disposed as coatings or as reinforcements, may be foamed. Also, the coatings, polymeric layers, and/or reinforcements may comprise closed-cell foams or open-celled foams. Open-celled foams, i.e., 15-50% volumetric air content, may be particularly effective for providing enhanced grip properties while closed-cell foams, 1-15% volumetric air content, may be particularly effective for providing use as impact bumpers, for example, on a back hand area of a glove.

A silkscreen printing process, as disclosed herein, allows the features to be applied in many different sizes, shapes, or patterns, as disclosed above, e.g., elliptical, circular, rectangular, as well as non-regular/asymmetrical patterns. At least one exemplary embodiment includes a silkscreen having a mesh size of approximately 40-61 threads per square inch, for example, for very viscous polyurethane solutions. For slightly less viscous polyurethane solutions, a silkscreen having a mesh size of approximately 86 threads per square inch may be used. The silkscreens comprise nylon screens, stainless steel screens, and/or polyester screens. In some embodiments, the fabric liners are dressed on an arcuate, glove-shaped former, stripped from the arcuate glove-shaped former, and dressed onto a flat glove shaped former for the screen-printing of reinforcements and/or other features on to polymeric layers, knitted fabrics, or both.

The knitted fabric liner 218 may be knitted from one or more yarns as discussed below, and may include one or more plaited layers. The knitted fabric liner 218 may be knitted by conventional knitting processes and comprise various yarns, deniers (such as from 70 denier to 800 denier), and gauges (10 gauge to 18 gauge). The knitted fabric liner 218, in accordance with embodiments of the invention, may be knitted using automatic seamless glove knitting machines. Seamless glove knitting machines include, but are not limited to, models NSFG, NSFG-I, SFG-1, and SWG by Shima Seiki Mfg., Ltd. Embodiments of the invention include fingers, palm, and cuffs that are tapered for a tighter fit. Knitting machines, including those manufactured and commercialized by Shima Seiki, Mfg., Ltd., as discussed below, can be programmed to accommodate a large number of changes in stitch dimensions using varied stitch setups and to alter the physical dimensions used for the knitted fabric liner 218, i.e., specified for finger length and width, palm length and width, and overall glove or liner length and width and the like. Some knitted liners have fabric knitted reinforcements in crotches of the liner, as disclosed in, for example, U.S. Pat. Nos. 7,434,422; 7,908,891, and/or US Publication No. 2011/0209505, which are commonly assigned and incorporated by reference in their entireties. In at least one embodiment disclosed herein, a knitted reinforcement has a polyurethane reinforcement disposed thereon. Also, according to at least one embodiment disclosed herein, a knitted reinforcement corresponds to an area having a polyurethane reinforcement disposed on a polymeric coating(s) thereon, e.g., both a knitted reinforcement and a polyurethane reinforcement are disposed on a crotch between the thumb and index finger, both are on the palm of a hand, both are on a knuckle region on a backhand.

The knitted fabric liner 218 comprises one or more of many different yarns and filaments to impart a variety of different properties to the fabric liners made therefrom. For example, cotton, wool, rayon, steel wire, glass fibers, filaments, ultra-high molecular weight polyethylene (UHMWPE), high-performance polyethylene (HPPE), such as DYNEEMA® and/or SPECTRA®, nylons, modacrylic yarns, oxidized-polyacrylonitrile (OPAN), meta-aramids, such as NOMEX®, para-aramids, such as KEVLAR® and/or TWARON®, aromatic polyesters, such as VECTRAN®, and the like, or any blend of these fibers and materials. Any yarn may comprise a blend of yarns, such as can be created by ring spun, rotor spun, friction spun, braiding, and other processes for blending yarns.

Some yarns may be used for cut-resistance, such as steel wire, glass fibers, filaments, ultra-high molecular weight polyethylene, NOMEX®, TWARON®, KEVLAR®, and DYNEEMA®. Other yarns provide dexterity and fit properties, such as stretchable yarns, for example, SPANDEX® and LYCRA®. Yarns capable of moisture management, such as STA-COOL® polyesters, HYDROTEC®, AQUARIUS®, and DRYENERGY®, may be included to withdraw moisture and perspiration from the skin, which also provide comfort. Furthermore, moisture and perspiration controlling yarns comprise antimicrobial agents, which are helpful in attenuating odors and/or preventing wounds and burns from becoming infected. Anti-microbial agents comprise surface coatings applied on the yarn, such as silane quaternary ammonium and/or N-Halamine compounds, TRICLOSAN®, as well as elemental silver and silver-releasing compounds.

Also, some yarns, for example, OPAN, such as PANOX®, and ARSELON®, provide enhanced flame- and/or heat-resistance. Also, some yarns may be plaited to create a liner having two or more layers. For example, a cut resistant yarn such as one or more of steel wire, glass fibers, filaments, ultra-high molecular weight polyethylene, nylons, NOMEX®, TWARON®, KEVLAR®, DYNEEMA®, SPECTRA®, VECTRAN®, and the like or any blend of these fibers and materials, may have an OPAN yarn or cotton fiber plaited therewith.

In at least one exemplary embodiment of the present invention, the knitted fabric liner 218 is an 18-gauge knitted structure comprising an aliphatic or aromatic nylon, an elastic fiber, fiberglass, and a cut-resistant yarn. In some embodiments of the present invention, the aliphatic nylon is nylon 66 and the aromatic nylon is an m-aramid, such as NOMEX® or a para-aramid, such as KEVLAR® or another polyphthalamide, the elastic fiber is an elastane, such as SPANDEX® or LYCRA®, and the cut-resistant yarn is an ultra-high molecular weight polyethylene fiber, such as DYNEEMA®.

Coagulant solutions, for example, a weak coagulant, such as a 1-20% wt. aqueous solution of acetic acid, formic acid, or tricarboxylic acid may be used in conjunction with the above methods. The coagulant solution penetrates substantially all of the entire thickness of the knitted fabric liner. When the coagulant coated fabric liner contacts the polymeric emulsion, the composition is destabilized and gels. Because the coagulant increases the gelling action of the elastomeric, polymeric, or latex emulsion, the ingress of the elastomeric, polymeric, or latex emulsion into the interstices of the liner is impeded, thereby substantially preventing "strike-through." Other suitable coagulants include, but are not limited to, strong coagulants, such as calcium nitrate, calcium chloride, calcium citrate, and the like, and other salts known to those in the art.

In some embodiments according to the invention, the knitted fabric liner and/or coated liner has a weak acid applied thereto, optionally followed by the application of a strong coagulant, as described in commonly-assigned patent application Ser. No. 13/928,615, which is herein incorporated by reference in its entirety. Without intending to be bound by theory, it is believed that first applying a weak acid gels the outer surface slowly, which allows the interior of the polymeric layer to receive the coagulant. Because the interior as well as the surface gels, the coating is not case hardened, as is the case with the application of a strong coagulant and is gelled more completely throughout the layer, and is therefore more abrasion-resistant.

At least one embodiment according to the present invention comprises a supported glove having at least one polymeric reinforcement, further comprising a fabric liner; a first polymeric emulsion adhered to at least a portion of the fabric liner, forming a first polymeric coating onto the fabric liner; and at least one polymeric reinforcement disposed on a portion of at least one of the polymeric coating, wherein the polymeric reinforcement comprises a polyurethane material. Embodiments according to the invention further comprise wherein the at least one polymeric reinforcement is disposed on the fabric liner, the first polymeric coating or both the fabric liner and the first polymeric coating. Embodiments according to the invention further comprise wherein the at least one polymeric reinforcement is disposed on a part of the fabric liner and a part of the first polymeric coating.

Furthermore, at least one embodiment according to the present invention of the supported glove disclosed above further comprises wherein the at least one polymeric reinforcement is disposed on a crotch and/or wherein the at least one polymeric reinforcement is disposed on a thumb crotch and/or wherein the at least one polymeric reinforcement is disposed on a crotch or the fabric liner and/or wherein the first polymeric emulsion comprises natural rubber polyisoprene, synthetic latexes, synthetic polyisoprene, carboxylated acrylonitrile butadiene, non-carboxylated acrylonitrile butadiene, butyl latex, polychloroprene, nitriles, aqueous-polyurethanes, non-aqueous-polyurethanes, or styrene-butadiene materials and/or wherein the polymeric reinforcement comprises an aqueous polyurethane material, a non-aqueous polyurethane material and/or wherein the polymeric reinforcement comprises a solution of a blend of a non-aqueous polyurethane material and a nitrile-butadiene material and/or wherein the polymeric reinforcement comprises a thermosetting polymeric material.

Additionally, at least one embodiment according to the present invention of an unsupported glove comprises a first polymeric emulsion disposed as a polymeric layer in the shape of a glove; at least one polymeric reinforcement disposed on a portion of the polymeric layer, wherein the polymeric reinforcement comprises a polyurethane material.

Furthermore, at least one embodiment of the unsupported glove described above further comprises wherein the at least one polymeric reinforcement is disposed on a crotch and/or wherein the at least one polymeric reinforcement is disposed on a thumb crotch and/or wherein the first polymeric emulsion comprises natural rubber polyisoprene, synthetic latexes, synthetic polyisoprene, carboxylated acrylonitrile butadiene, non-carboxylated acrylonitrile butadiene, butyl latex, polychloroprene, nitriles, aqueous-polyurethanes, non-aqueous-polyurethanes, or styrene-butadiene materials and/or wherein the polymeric reinforcement comprises an aqueous polyurethane, a non-aqueous polyurethane material and/or wherein the polymeric reinforcement comprises a solution of a blend of a non-aqueous polyurethane material and a nitrile-butadiene material.

Any glove described herein, whether supported or unsupported, may be made by a method of making a reinforced glove, comprising the steps of dipping a glove-shaped former into a polymeric emulsion, forming a polymeric layer in the shape of a glove; curing the polymeric layer; placing the polymeric layer on a flat former; screen-printing a polymeric reinforcement on the polymeric layer; and heating the reinforcement to cure the reinforcement, wherein a reinforced glove is formed.

Any glove made by a silk-screening process, as described above may further comprise wherein the screen-printing step comprises a silkscreen having a mesh size of approximately 40-61 threads per square inch or a silkscreen having a mesh size of approximately 86 threads per square inch. Moreover, any polymeric reinforcement, which may be foamed as is known to those in the art, may comprise a solution of non-aqueous polyurethane material or a blend of a non-aqueous polyurethane material and a nitrile-butadiene material.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in any one or more of the embodiments. Also, it is to be understood that polymeric, elastomeric, and latex are used interchangeably herein with respect to polymeric coatings and raised features made from polymeric compositions.

While the foregoing is directed to embodiments of the present invention, other and further embodiments of the invention may be devised without departing from the basic scope thereof, and the scope thereof is determined by the claims that follow.

What is claimed is:

1. An unsupported glove having at least one polymeric reinforcement, the unsupported glove comprising: a first polymeric emulsion disposed as a polymeric layer in the shape of a glove; and at least one polymeric reinforcement screen printed on a portion of the polymeric layer, wherein the polymeric reinforcement comprises a polyurethane material.

2. The unsupported glove of claim 1, wherein the at least one polymeric reinforcement is screen printed on at least one finger crotch.

3. The unsupported glove of claim 1, wherein the at least one polymeric reinforcement is screen printed on a thumb crotch.

4. The unsupported glove of claim 1, wherein the polymeric reinforcement comprises a non-aqueous polyurethane material.

5. The unsupported glove of claim 1, wherein the polymeric reinforcement comprises a solution of a blend of a non-aqueous polyurethane material and a nitrile-butadiene material.

6. The unsupported glove of claim 1, wherein the first polymeric emulsion comprises natural rubber polyisoprene, synthetic latexes, synthetic polyisoprene, carboxylated acrylonitrile butadiene, non-carboxylated acrylonitrile butadiene, butyl latex, polychloroprene, nitriles, aqueous-polyurethanes, non-aqueous-polyurethanes, or styrene-butadiene materials.

7. The unsupported glove of claim 1, wherein the polymeric reinforcement is a silkscreen-printed layer that covers an area of the polymeric layer limited to reinforce a thumb crotch.

8. The unsupported glove of claim 1, wherein the at least one polymeric reinforcement is screen printed on the portion of the polymeric layer using a silkscreen having a mesh size of approximately 40-61 threads per square inch.

9. The unsupported glove of claim 1, wherein the at least one polymeric reinforcement is screen printed on the portion of the polymeric layer using a silkscreen having a mesh size of approximately 86 threads per square inch.

* * * * *

UNITED STATES PATENT AND TRADEMARK OFFICE
CERTIFICATE OF CORRECTION

| | |
|---|---|
| PATENT NO. | : 11,805,830 B2 |
| APPLICATION NO. | : 17/833483 |
| DATED | : November 7, 2023 |
| INVENTOR(S) | : Marco Antonio Francisco Costa et al. |

It is certified that error appears in the above-identified patent and that said Letters Patent is hereby corrected as shown below:

On the Title Page

In the abstract, item (57), Line 4, please delete "ac parts(s)" and substitute "a part(s)"

Signed and Sealed this
Twenty-sixth Day of March, 2024

Katherine Kelly Vidal
*Director of the United States Patent and Trademark Office*